United States Patent
Nakayama et al.

(10) Patent No.: US 11,273,237 B2
(45) Date of Patent: Mar. 15, 2022

(54) METHOD FOR PRODUCING POROUS SUBSTRATE COMPRISING BIOABSORBABLE POLYMER THAT CONTAINS HEPARIN, POROUS SUBSTRATE COMPRISING BIOABSORBABLE POLYMER THAT CONTAINS HEPARIN, AND ARTIFICIAL BLOOD VESSEL

(71) Applicant: GUNZE LIMITED, Ayabe (JP)

(72) Inventors: Hidetaka Nakayama, Kyoto (JP); Toshiharu Shinoka, Tokyo (JP); Shuhei Tara, Tokyo (JP); Tadahisa Sugiura, Tokyo (JP)

(73) Assignee: GUNZE LIMITED, Kyoto (JP)

( * ) Notice: Subject to any disclaimer, the term of this patent is extended or adjusted under 35 U.S.C. 154(b) by 463 days.

(21) Appl. No.: 16/334,578

(22) PCT Filed: Aug. 31, 2017

(86) PCT No.: PCT/JP2017/031406
§ 371 (c)(1),
(2) Date: Mar. 19, 2019

(87) PCT Pub. No.: WO2018/056018
PCT Pub. Date: Mar. 29, 2018

(65) Prior Publication Data
US 2021/0283314 A1    Sep. 16, 2021

(30) Foreign Application Priority Data

Sep. 21, 2016    (JP) .............................. JP2016-184313

(51) Int. Cl.
*A61L 27/56*    (2006.01)
*A61L 27/14*    (2006.01)
(Continued)

(52) U.S. Cl.
CPC ............... *A61L 27/56* (2013.01); *A61L 27/14* (2013.01); *A61L 27/507* (2013.01); *A61L 27/54* (2013.01);
(Continued)

(58) Field of Classification Search
CPC ........ A61L 27/56; A61L 27/14; A61L 27/507; A61L 27/54; A61L 27/58;
(Continued)

(56) References Cited

U.S. PATENT DOCUMENTS

2002/0010482 A1 *   1/2002   Watt ................. A61B 17/07292
                                                         606/151
2014/0377217 A1 * 12/2014   Matheny ............ A61K 31/5377
                                                         424/85.2
(Continued)

FOREIGN PATENT DOCUMENTS

| CN | 101068865 | 11/2007 |
| CN | 101330905 | 12/2008 |

(Continued)

OTHER PUBLICATIONS

Chen, et al., "Electrospun poly(I-lactic acid-co-E-caprolactone) fibers loaded with heparin and vascular endothelial growth factor to improve blood compatibility and endothelial progenitor cell proliferation" Colloids and Surfaces B: Biointerfaces 128 (2015) 106-114.

(Continued)

*Primary Examiner* — Nahida Sultana
(74) *Attorney, Agent, or Firm* — Hamre, Schumann, Mueller & Larson, P.C.

(57) ABSTRACT

The present invention aims to provide a method for producing a porous substrate containing a bioabsorbable polymer and heparin in a simple manner without use of a surfactant, a porous substrate containing a bioabsorbable polymer and (Continued)

heparin, and an artificial blood vessel. The present invention provides a method for producing a porous substrate containing a bioabsorbable polymer and heparin, including: a solution preparing step of preparing a heparin-bioabsorbable polymer solution having heparin uniformly dispersed therein and a bioabsorbable polymer dissolved therein, using the bioabsorbable polymer, the heparin, a solvent 1 that is a poor solvent having a lower solvency for the bioabsorbable polymer, a solvent 2 that is a good solvent having a higher solvency for the bioabsorbable polymer and is incompatible with the solvent 1, and a common solvent 3 compatible with the solvent 1 and the solvent 2; a precipitating step of cooling the heparin-bioabsorbable polymer solution to precipitate a porous body containing the bioabsorbable polymer and the heparin; and a freeze-drying step of freeze-drying the porous body containing the bioabsorbable polymer and the heparin to provide a porous substrate containing the heparin.

2 Claims, 2 Drawing Sheets

(51) Int. Cl.
A61L 27/50 (2006.01)
A61L 27/54 (2006.01)
A61L 27/58 (2006.01)
B29C 67/20 (2006.01)
B29K 67/00 (2006.01)
B29K 105/00 (2006.01)
B29L 31/00 (2006.01)

(52) U.S. Cl.
CPC ............ *A61L 27/58* (2013.01); *B29C 67/20* (2013.01); *A61L 2300/236* (2013.01); *B29K 2067/04* (2013.01); *B29K 2105/0035* (2013.01); *B29K 2995/006* (2013.01); *B29L 2031/7534* (2013.01)

(58) Field of Classification Search
CPC ... A61L 2300/236; A61L 27/50; B29C 67/20; B29C 67/202; B29K 2067/04; B29K 2105/0035; B29K 2995/006; B29L 2031/7534
See application file for complete search history.

(56) References Cited

U.S. PATENT DOCUMENTS

| | | | |
|---|---|---|---|
| 2016/0215072 A1* | 7/2016 | Cool | A61L 27/20 |
| 2019/0263068 A1* | 8/2019 | Mannarino | B33Y 10/00 |

FOREIGN PATENT DOCUMENTS

| | | |
|---|---|---|
| CN | 103263672 | 8/2013 |
| EP | 1 860 142 | 11/2007 |
| JP | 5-184662 | 7/1993 |
| JP | 2011-212437 | 10/2011 |
| JP | 2016-158765 | 9/2016 |
| WO | 2007/061529 | 5/2007 |
| WO | 2008/045021 | 4/2008 |

OTHER PUBLICATIONS

Zhu, et al., "Fabrication of highly interconnected porous silk fibroin scaffolds for potential use as vascular grafts", Acta Biomaterialia, vol. 10, 2014, pp. 2014-2023.

* cited by examiner (a)

(b)

METHOD FOR PRODUCING POROUS SUBSTRATE COMPRISING BIOABSORBABLE POLYMER THAT CONTAINS HEPARIN, POROUS SUBSTRATE COMPRISING BIOABSORBABLE POLYMER THAT CONTAINS HEPARIN, AND ARTIFICIAL BLOOD VESSEL

TECHNICAL FIELD

The present invention relates to a method for producing a porous substrate containing a bioabsorbable polymer and heparin in a simple manner without use of a surfactant, a porous substrate containing a bioabsorbable polymer and heparin, and an artificial blood vessel.

BACKGROUND ART

Recent advances in the cell engineering have enabled culturing of various animal cells, including human cells. Research on the reconstruction of human tissues or organs using such cells, that is, what is called regenerative medicine, is progressing rapidly.

For example, the most frequently used artificial blood vessels in clinic are those containing non-absorbable polymers, such as GORE-TEX. Unfortunately, artificial blood vessels containing non-absorbable polymers remain as foreign matter in the body for a long time after grafting, so that anti-coagulants and the like have to be continuously administered. In addition, when such artificial blood vessels are used in children, repeat surgery is disadvantageously required as they grow older. To overcome the situation, regeneration of blood vessel tissue by regenerative medicine has been attempted.

The point of regenerative medicine is whether cells can grow and differentiate into a three-dimensional, living tissue-like structure. In an exemplary method, a substrate is implanted into the patient's body so that cells from the surrounding tissue or organ can enter the substrate and grow and differentiate to regenerate tissue or an organ.

Porous substrates containing bioabsorbable polymers have been proposed as the substrates for regenerative medicine. When a porous substrate containing a bioabsorbable polymer is used as the substrate for regenerative medicine, cells enter the voids in the substrate and grow, thus rapidly regenerating tissue. In addition, such substrates are decomposed and absorbed in the living body after a certain period of time, thus do not need to be removed by repeat surgery.

Prevention of thrombus formation is also important for the regeneration of blood vessel tissue by regenerative medicine. Thrombus formation often causes clogging of blood vessels, particularly in regeneration of small-diameter blood vessel tissue. Such clogging not only prevents regeneration of normal blood vessels, but also may cause severer symptoms.

A method that has been employed to prevent thrombus formation is to incorporate heparin into a porous substrate containing a bioabsorbable polymer and slowly release the heparin with decomposition of the porous substrate.

For example, Non-Patent Literature 1 discloses such a porous substrate containing a bioabsorbable polymer and heparin. Specifically, Non-Patent Literature 1 discloses a method for producing a nanofiber material for blood vessels, wherein an aqueous heparin sodium solution and a surfactant are added to an organic solvent having a bioabsorbable polymer dissolved therein, and the resulting micellar solution is used to produce the nanofiber material.

However, the porous substrate containing a bioabsorbable polymer and heparin disclosed in Non-Patent Literature 1 hinders regeneration of blood vessel tissue as it contains a highly toxic surfactant. Other methods have been studied for producing a porous substrate containing a bioabsorbable polymer and heparin, but those methods are very complicated or denature heparin during the production process, thus failing to provide the desired thrombus formation-preventing effect.

CITATION LIST

Non-Patent Literature

Non-Patent Literature 1: Colloids and Surfaces B: Biointerfaces, 128(2015), 106-114

SUMMARY OF INVENTION

Technical Problem

In view of the situation in the art, the present invention aims to provide a method for producing a porous substrate containing a bioabsorbable polymer and heparin in a simple manner without use of a surfactant, a porous substrate containing a bioabsorbable polymer and heparin, and an artificial blood vessel.

Solution to Problem

The present invention is directed to a method for producing a porous substrate containing a bioabsorbable polymer and heparin, including: a solution preparing step of preparing a heparin-bioabsorbable polymer solution having heparin uniformly dispersed therein and a bioabsorbable polymer dissolved therein, using the bioabsorbable polymer, the heparin, a solvent 1 that is a poor solvent having a lower solvency for the bioabsorbable polymer, a solvent 2 that is a good solvent having a higher solvency for the bioabsorbable polymer and is incompatible with the solvent 1, and a common solvent 3 compatible with the solvent 1 and the solvent 2; a precipitating step of cooling the heparin-bioabsorbable polymer solution to precipitate a porous body containing the bioabsorbable polymer and the heparin; and a freeze-drying step of freeze-drying the porous body containing the bioabsorbable polymer and the heparin to provide a porous substrate containing the heparin.

The present invention is described in detail below.

For porous substrates containing bioabsorbable polymers, control of their properties such as pore size and bulk density is extremely important from the standpoint of mechanical strength as a tissue regeneration scaffold, bioabsorption behavior, cell permeability, supply of nutrition to cells entering the substrate, and the like. A known process for producing such a porous substrate containing a bioabsorbable polymer is the phase separation process, which includes forming a homogenous phase by mixing a good solvent and a poor solvent for the bioabsorbable polymer, followed by cooling to give a porous body. In the phase separation process, the pore size of the resulting porous substrate can be adjusted by adjustment of the mixing ratio between the good solvent and the poor solvent. However, the adjustment of the pore size of the porous substrate in the phase separation process greatly changes the bulk density of the resulting porous substrate. Specifically, for production of a porous substrate having a large pore size, the ratio of the poor solvent has to be high. This makes the ratio of the good solvent relatively low, so that the resulting porous substrate has a high bulk density. Conversely, for production of a porous substrate having a small pore size, the ratio of the good solvent is set high and that of the poor solvent set low, so that the resulting porous substrate has a low bulk density. It is thus very difficult to produce a porous substrate having a different pore size but the same bulk density by the phase separation process. Furthermore, the phase separation process requires that the good solvent and the poor solvent are compatible with each other. When water, which is easy to handle, is selected as the poor solvent, there are only limited choices of good solvents such as 1,4-dioxane, N-methylpyrrolidone, and dimethyl sulfoxide. These solvents are highly toxic to the living body, and thus a step for completely removing the solvents from the porous substrates is required for clinical application. This disadvantageously makes the production process complicated.

The present inventors made intensive studies to devise a method for producing a porous substrate in which good and poor solvents for a bioabsorbable polymer are used in combination with a common solvent compatible with both of the good and poor solvents. With the common solvent, the good solvent and the poor solvent do not have to be compatible with each other. This allows a much wider choice of combinations of good solvents and poor solvents. In addition, in the production method, a less toxic organic solvent other than 1,4-dioxane, N-methylpyrrolidone, or dimethyl sulfoxide can be selected as the good solvent. Furthermore, the bulk density and pore size of the porous substrate can be easily adjusted by combining two or more common solvents and adjusting the mixing ratio between the two or more common solvents.

The present inventors focused on the fact that the poor solvent for the bioabsorbable polymer can dissolve heparin. They found out that by dissolving heparin in the poor solvent in advance, a porous substrate containing a bioabsorbable polymer and heparin can be produced in a very simple manner without use of a surfactant. They thus completed the present invention.

In the method for producing a porous substrate containing a bioabsorbable polymer and heparin of the present invention (hereinafter also referred to as simply a "method for producing a porous substrate"), first, a solution preparing step is performed. In this step, a heparin-bioabsorbable polymer solution having heparin uniformly dispersed therein and a bioabsorbable polymer dissolved therein is prepared using the bioabsorbable polymer, the heparin, a solvent 1, a solvent 2, and a common solvent 3.

Examples of the bioabsorbable polymer include synthetic polymers such as polyglycolide, polylactide, poly-ε-caprolactone, lactide-glycolic acid copolymer, glycolide-ε-caprolactone copolymer, lactide-ε-caprolactone copolymer, polycitric acid, polymalic acid, poly-α-cyanoacrylate, poly-β-hydroxy acid, polytrimethylene oxalate, polytetramethylene oxalate, polyorthoester, polyorthocarbonate, polyethylene carbonate, poly-γ-benzyl-L-glutamate, poly-γ-methyl-L-glutamate, poly-L-alanine, polyglycol, and sebacic acid, polysaccharides such as starch, alginic acid, hyaluronic acid, chitin, pectic acid, and derivatives thereof, and natural polymers such as proteins (e.g., gelatin, collagen, albumin, fibrin). These bioabsorbable materials may be used alone or in combination of two or more thereof.

The heparin is a drug known as an anticoagulant that activates antithrombin and suppresses the coagulation system through activation of anticoagulant activity. Conventionally known heparin may be used. Warfarin, which is an anticoagulant, and aspirin and dipyridamole, which are antiplatelets, can be used as well as heparin.

The solvent 1 is a poor solvent having a lower solvency for the bioabsorbable polymer. The "poor solvent" as used herein means that the solvent is less likely to dissolve the bioabsorbable polymer than the solvent 2 is, and more specifically means that the mass of the bioabsorbable polymer that dissolves in 100 g of the solvent 1 at a room temperature of 25° C. is 0.01 g or less.

In cases where the bioabsorbable polymer is a synthetic polymer, the solvent 1 may be water, methanol, n-propanol, isopropanol, or n-butanol, for example. In particular, water is suitable because it has excellent handleability and well dissolves heparin.

The solvent 2 is a good solvent having a higher solvency for the bioabsorbable polymer. The "good solvent" as used herein means that the solvent is more likely to dissolve the bioabsorbable polymer than the solvent 1 is, and more specifically means that the mass of the bioabsorbable polymer that dissolves in 100 g of the solvent 2 at a room temperature of 25° C. is 0.1 g or more.

The solvent 2 is incompatible with the solvent 1. The "incompatible" as used herein means that phase separation occurs even after mixing and stirring at a room temperature of 25° C.

In cases where the bioabsorbable polymer is a synthetic polymer and water is selected as the solvent 1, the solvent 2 may be an organic solvent such as methyl ethyl ketone, diethyl ketone, methyl propyl ketone, methyl isobutyl ketone, methylamino ketone, cyclohexanone, chloroform, ethyl acetate, or toluene. In particular, for example, methyl ethyl ketone and chloroform are suitable because they have relatively low toxicity.

The common solvent 3 is compatible with both of the solvent 1 and the solvent 2. Combining such a common solvent 3 with the solvent 1 and the solvent 2 enables production of a porous substrate by the phase separation process even if the solvent 1 and the solvent 2 are incompatible with each other. This remarkably widens the choice of combinations of the solvents 1 and 2. The "compatible" as used herein means that phase separation does not occur even after mixing and stirring at a room temperature of 25° C.

In cases where the bioabsorbable polymer is a synthetic polymer and water and an organic solvent are selected as the solvent 1 and the solvent 2 respectively, the common solvent 3 may be, for example, acetone, methanol, ethanol, propanol, isopropanol, n-butanol, 2-butanol, isobutanol, or tetrahydrofuran.

The mixing ratio between the solvent 1 and the solvent 2 is not limited. Preferably, the weight ratio between the solvent 1 and the solvent 2 is within the range of 1:1 to 1:100. With the weight ratio within this range, a uniform porous substrate can be produced. The weight ratio is more preferably within the range of 1:10 to 1:50.

The mixing ratio between the total of the solvent 1 and the solvent 2 and the common solvent 3 is not limited. Preferably, the weight ratio between the total of the solvent 1 and the solvent 2 and the common solvent 3 is within the range of 1:0.01 to 1:0.5. With the weight ratio within this range, a uniform porous substrate can be produced. The weight ratio is more preferably within the range of 1:0.02 to 1:0.3.

The pore size of the resulting porous substrate can be controlled by adjusting the mixing ratio between the solvent 1 and the solvent 2. Specifically, an increase in the ratio of the solvent 1 increases the pore size of the resulting porous substrate, and an increase in the ratio of the solvent 2 decreases the pore size of the resulting porous substrate. However, the control of the pore size by the method of adjusting the mixing ratio between the solvent 1 and the solvent 2 unfortunately changes the bulk density at the same time. It is thus difficult to produce a porous substrate having desired pore size and bulk density by this method.

Thus, in the method for producing a porous substrate of the present invention, two or more common solvents 3 are preferably used in combination (hereinafter, the two or more solvents included in the common solvent 3 are also referred to as a "common solvent 3-1", a "common solvent 3-2", . . . ). The pore size of the resulting porous substrate can be controlled by combining two or more common solvents 3, for example, a common solvent 3-1 and a common solvent 3-2, and adjusting the mixing ratio between these solvents. In other words, the pore size of the resulting porous substrate can be controlled by adjusting the mixing ratio between the common solvent 3-1 and the common solvent 3-2 included in the common solvent 3 while holding the mixing ratio between the solvent 1, the solvent 2, and the common solvent 3 constant. This means that the bulk density of the resulting porous substrate can remain substantially constant while only the pore size is adjusted. This method for producing a porous substrate of the present invention makes it easy to produce a porous substrate having desired pore size and bulk density.

The combination of the bioabsorbable polymer and the solvents is not limited. Examples of the combination include: a combination of a lactide-ε-caprolactone copolymer as the bioabsorbable polymer with water as the solvent 1, methyl ethyl ketone as the solvent 2, acetone as the common solvent 3-1, and ethanol as the common solvent 3-2; a combination of polylactide as the bioabsorbable polymer with water as the solvent 1, chloroform as the solvent 2, tetrahydrofuran as the common solvent 3-1, and ethanol as the common solvent 3-2; and a combination of polylactide as the bioabsorbable polymer with water as the solvent 1, chloroform as the solvent 2, acetone as the common solvent 3-1, and ethanol as the common solvent 3-2.

In the solution preparing step, a heparin-bioabsorbable polymer solution having heparin uniformly dispersed therein and a bioabsorbable polymer dissolved therein is prepared using the bioabsorbable polymer, the heparin, the solvent 1, the solvent 2, and the common solvent 3.

Specific examples of the method for preparing the heparin-bioabsorbable polymer solution include a method involving dissolving heparin in the solvent 1, mixing the bioabsorbable polymer with a solvent mixture (hereinafter also referred to simply as a "solvent mixture") containing the solvent 1 having the heparin dissolved therein, the solvent 2, and the common solvent 3, followed by heating. Simpler methods for preparing the heparin-bioabsorbable polymer solution include a method involving heating the solvent mixture and adding the bioabsorbable polymer to the heated solvent mixture; and a method involving dissolving the bioabsorbable polymer in the solvent 2 and then adding the solvent 1 having the heparin dissolved therein and the common solvent 3 to the solvent 2 with heating.

The mixing method is not limited. For example, a known mixing method using stirrer chips or stirring bars may be used.

The obtained heparin-bioabsorbable polymer solution has the bioabsorbable polymer uniformly dissolved therein and the heparin uniformly dispersed therein. The heparin in the heparin-bioabsorbable polymer solution seemingly forms stable micelles by self-micellization.

The heating temperature in the solution preparing step may be any temperature at which the bioabsorbable polymer is uniformly dissolved. Preferably, the heating temperature is lower than the boiling point of any of the solvent 1, the solvent 2, and the common solvent 3. Heating to the boiling point or higher may vary the mixing ratio between the solvents, which may make it impossible to control the pore size and bulk density of the resulting porous substrate.

In the method for producing a porous substrate of the present invention, next, a precipitating step is performed. In this step, the heparin-bioabsorbable polymer solution is cooled to precipitate a porous body containing the bioabsorbable polymer and the heparin. Cooling the heparin-bioabsorbable polymer solution precipitates a porous body containing the bioabsorbable polymer that has become insoluble. This is presumably because, before the bioabsorbable polymer crystallizes and precipitates, phase separation (liquid-liquid phase separation) of the bioabsorbable polymer in the liquid state and the solvents occurs due to thermodynamic instability at a temperature higher than the temperature at which the bioabsorbable polymer crystallizes. At this time, the heparin dispersed in the heparin-bioabsorbable polymer solution uniformly adheres, by van der Waals forces or the like, to the surface of the precipitated porous body containing the bioabsorbable polymer.

The cooling temperature in the precipitating step may be any temperature at which the porous body containing the bioabsorbable polymer can precipitate. Preferably, the temperature is 4° C. or lower, more preferably −24° C. or lower.

The cooling rate also affects the pore size of the resulting porous substrate. Specifically, a higher cooling rate tends to result in a smaller pore size, and a slower cooling rate tends to result in a larger pore size. Thus, especially for production of a porous substrate having a small pore size, the cooling temperature may be set low to rapidly cool the heparin-bioabsorbable polymer solution.

In the method for producing a porous substrate of the present invention, next, a freeze-drying step is performed. In this step, the obtained porous body containing the bioabsorbable polymer and the heparin is freeze-dried to give a porous substrate containing the heparin.

The freeze-drying may be performed under any conditions, and may be performed under conventionally known conditions.

The freeze-drying step may be performed after the cooling step without any further treatment; however, for removal of organic solvents used as the solvents, the porous body may be immersed in a solvent such as ethanol to replace the organic solvents before freeze-drying. The solvent used at this time is one that does not dissolve heparin so that the heparin does not dissolve out of the porous substrate.

Use of the method for producing a porous substrate of the present invention enables production of a porous substrate containing a bioabsorbable polymer and heparin in a very simple manner without use of a highly toxic surfactant. Use of the method also enables production of a porous substrate with easy adjustment of the bulk density and the pore size and without use of a highly toxic solvent.

The present invention is also directed to a porous substrate containing heparin produced by the method for producing a porous substrate containing heparin of the present invention.

The porous substrate containing heparin of the present invention is free of a surfactant despite containing heparin. Thus, regeneration of tissue such as blood vessels is not hindered by the toxicity of a surfactant.

Herein, the phrase "free of a surfactant" means that the surfactant content is 0.1 ppm or less.

The porous substrate containing a bioabsorbable polymer and heparin of the present invention can be used for regeneration of blood vessels, neurons, and the like, particularly suitably used for regeneration of blood vessels.

In particular, a tubular artificial blood vessel produced by the method for producing a porous substrate of the present invention can exhibit excellent performance.

In the following, the production of an artificial blood vessel by the method for producing a porous substrate of the present invention is described in more detail.

The method for producing a tubular artificial blood vessel includes a solution preparing step, a precipitating step, and a freeze-drying step performed in the stated order, as the method for producing a porous substrate of the present invention. The method for producing a tubular artificial blood vessel includes a step for forming a tubular shape after the solution preparing step and before the precipitating step.

Specifically, an application step is performed. In this step, the heparin-bioabsorbable polymer solution obtained in the solution preparing step is applied to a surface of a rod-shaped body. Thereafter, the precipitating step is performed. In the precipitating step, the heparin-bioabsorbable polymer solution on the surface of the rod-shaped body is cooled to precipitate a tubular porous body containing the bioabsorbable polymer and the heparin around the rod-shaped body.

The rod-shaped body is a member used for forming the porous body in a tubular shape. The diameter of the rod-shaped body substantially corresponds to the inner diameter of the tubular artificial blood vessel obtained when the rod-shaped body is pulled out from the obtained porous body.

The present inventors found out that especially in cases where the rod-shaped body is a rod-shaped body containing a metal such as stainless steel or resin-coated stainless steel, the resulting tubular artificial blood vessel allows, when grafted, regeneration of a quite normal blood vessel less susceptible to hypertrophy and calcification.

The reason for this is presumably as follows. In the precipitating step of cooling the heparin-bioabsorbable polymer solution on the surface of the rod-shaped body to precipitate a porous body containing the bioabsorbable polymer and the heparin around the rod-shaped body, the inner portion of the tube in contact with the rod-shaped body containing a highly thermally conductive metal is rapidly cooled, thus forming a layer (hereinafter, also referred to as a "skin layer") having a relatively small pore size as compared with the surrounding portion (hereinafter, also referred to as a "porous layer"). For blood vessel regeneration, the artificial blood vessel as a whole needs to have pores with a pore size sufficient for entrance of cells. On the inner portion, which directly contacts blood flow, however, it is important to prevent deposition of platelets, a cause of hypertrophy and calcification. The formation of the skin layer on the inner side of the tubular artificial blood vessel prevents the deposition of platelets on the inner portion that contacts with blood flow, while allowing easy entrance of cells in other portions. This presumably leads to the regeneration of a quite normal blood vessel.

It is also possible, by adjusting the type of the rod-shaped body, the method for cooling the rod-shaped body, and the like, to produce an artificial blood vessel in which the skin layer is on the inner side and the pore size of the porous layer around the skin layer increases outward. Conversely, it is also possible to produce an artificial blood vessel in which the skin layer is on the outer side and the pore size of the porous layer inside the skin layer increases inward.

The heparin-bioabsorbable polymer solution may be applied to the surface of the rod-shaped body by any method. Examples of the method include a method involving dipping the rod-shaped body into the heparin-bioabsorbable polymer solution one or two or more times; and a method involving placing the rod-shaped body in a tubular body having an inner diameter larger than the diameter of the rod-shaped body and pouring the heparin-bioabsorbable polymer solution into the gap between the rod-shaped body and the tubular body.

Since the resulting tubular porous body slightly shrinks in the precipitating step, the rod-shaped body and the tubular body are easily pulled out; however, the surface of the rod-shaped body and the tubular body may be subjected to smoothing treatment such as coating in advance.

The present invention is also directed to an artificial blood vessel containing the porous substrate containing heparin of the present invention. The inner diameter of the artificial blood vessel of the present invention is not limited. From the standpoint of the inner diameter of typical blood vessels, the lower limit of the inner diameter is preferably 0.5 mm, and the upper limit thereof is preferably about 8.0 mm. The outer diameter of the artificial blood vessel is not limited. From the standpoint of the outer diameter of typical blood vessels, the lower limit of the outer diameter is preferably 1.0 mm, and the upper limit thereof is preferably about 10.0 mm.

Artificial blood vessels usable for peripheral blood vessels having an inner diameter of about 2.0 to 5.0 mm are particularly difficult to produce by conventional methods. Such artificial blood vessels, however, can be easily produced by the method for producing a porous substrate of the present invention.

The artificial blood vessel of the present invention preferably includes, as an outermost layer, an ultrafine fiber nonwoven fabric layer containing ultrafine fibers. The ultrafine fibers contain a bioabsorbable polymer and have a fiber size of 0.1 to 10 µm. Formation of such an ultrafine fiber nonwoven fabric layer as an outermost layer prevents leakage of blood due to blood flow pressure. The ultrafine fiber nonwoven fabric layer also exhibits sufficient strength against external pressure after grafting, and thus can prevent blockage of the blood vessel due to kinking.

The bioabsorbable polymer constituting the ultrafine fiber nonwoven fabric layer is not limited. For example, any of the above synthetic polymers, natural polymers, and the like may be used.

In particular, two or more bioabsorbable polymers different in bioabsorbability are preferably used in combination as the bioabsorbable polymer constituting the ultrafine fiber nonwoven fabric layer. While the ultrafine fiber nonwoven fabric layer improves the strength of the artificial blood vessel, it can prevent the entrance of the cells and thereby delay blood vessel regeneration or cause calcification. This can be remarkably improved by combining two or more bioabsorbable polymers different in bioabsorbability to constitute the ultrafine fiber nonwoven fabric layer.

For example, polyglycolide having a relatively high bioabsorbability and polylactide having a relatively low bioabsorbability may be combined to constitute the ultrafine fiber nonwoven fabric layer. In this case, neither of the two bioabsorbable polymers decomposes in the relatively early period just after grafting when strength is particularly required. Thus, a high strength-improving effect can be exhibited. Thereafter, voids are formed in the ultrafine fiber nonwoven fabric layer as the polyglycolide having a relatively high bioabsorbability is gradually decomposed and absorbed. These voids allow easy entrance of cells, leading to promotion of blood vessel regeneration and prevention of calcification.

The lower limit of the thickness of the ultrafine fiber nonwoven fabric layer is preferably 10 μm, and the upper limit thereof is preferably 1000 μm. With the thickness of the ultrafine fiber nonwoven fabric layer within this range, a sufficient strength-improving effect can be obtained.

The ultrafine fiber nonwoven fabric layer may be formed by any method, but preferably formed by electrospinning. Electrospinning is a method involving discharging a solution having a bioabsorbable polymer dissolved therein from a nozzle to a target while applying high voltage between the nozzle and a collector electrode. The solution ejected from the nozzle is formed into the shape of ultrafine fibers along the lines of electric force, and deposits onto the target.

In the method for producing an artificial blood vessel of the present invention, when the rod-shaped body used is a conductive rod-shaped body containing a metal, the rod-shaped body can be used as the collector electrode. In this case, the ultrafine fiber nonwoven fabric layer can be formed as the outermost layer of the tubular artificial blood vessel by discharging the solution while rotating the rod-shaped body with the tubular artificial blood vessel therearound and reciprocating the nozzle multiple times.

Advantageous Effects of Invention

The present invention can provide a method for producing a porous substrate containing a bioabsorbable polymer and heparin in a simple manner without use of a surfactant, a porous substrate containing a bioabsorbable polymer and heparin, and an artificial blood vessel.

DESCRIPTION OF EMBODIMENTS

Figure 1:
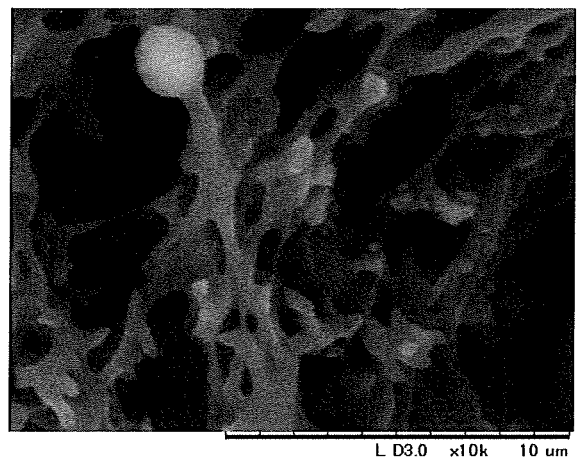
FIG. 1 shows cross-sectional electron micrographs of porous substrates obtained in Example 1 and Comparative Example 1.
Figure 1:
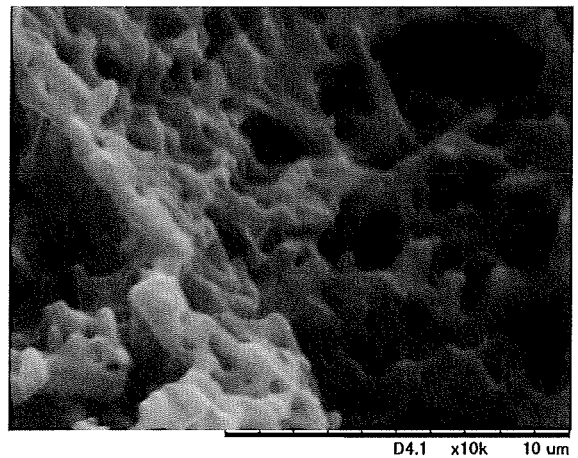

The embodiments of the present invention are described in more detail with reference to examples. The present invention however is not limited to these examples.

Example 1

At a room temperature of 25° C., 0.25 g of a L-lactide-ε-caprolactone copolymer (molar ratio: 50:50) was mixed with a mixed solution containing: 0.3 mL of water having heparin (Wako Pure Chemical Industries, Ltd., JIS guaranteed reagent) dissolved therein at a concentration of 7200 units/mL as the solvent 1; 2.0 mL of methyl ethyl ketone as the solvent 2; and 1.0 mL of acetone as the common solvent 3. Thus, a non-uniform solution not dissolving the L-lactide-ε-caprolactone copolymer was obtained. The heparin in the non-uniform solution did not precipitate and formed stable micelles.

Subsequently, the obtained non-uniform solution was put in a glass tube having a diameter of 3.3 mm and heated at 60° C. to give a solution containing the heparin uniformly dispersed therein and the L-lactide-ε-caprolactone copolymer dissolved therein.

The obtained uniform solution was then cooled to 4° C. or −24° C. in a freezer to precipitate a porous body containing the L-lactide-ε-caprolactone copolymer and heparin.

The obtained porous body was immersed in an ethanol bath (50 mL) at 4° C. or −24° C. for 12 hours, and then immersed in a water bath (50 mL) at 25° C. for 12 hours for washing.

Thereafter, the porous body was freeze-dried at −40° C. to give a cylindrical porous substrate having a diameter of 3.0 mm and a height of 15 mm.

Example 2

A porous substrate was produced as in Example 1 except that a solvent mixture of 0.5 mL of acetone (common solvent 3-1) and 0.5 mL of ethanol (common solvent 3-2) was used as the common solvent 3.

The heparin in the obtained non-uniform solution did not precipitate and formed stable micelles.

Example 3

At a room temperature of 25° C., 0.25 g of an L-lactide-ε-caprolactone copolymer (molar ratio: 50:50) was mixed with a mixed solution containing: 0.2 mL of water having heparin (Wako Pure Chemical Industries, Ltd., JIS guaranteed reagent) dissolved therein at a concentration of 7200 units/mL as the solvent 1; 2.5 mL of methyl ethyl ketone as the solvent 2; and 0.8 mL of acetone and 0.2 mL of ethanol as the common solvent 3. Thus, a non-uniform solution not dissolving the L-lactide-ε-caprolactone copolymer was obtained. The heparin in the obtained non-uniform solution did not precipitate and formed stable micelles.

Subsequently, the obtained non-uniform solution was heated at 60° C. to give a uniform solution containing the heparin uniformly dispersed therein and the L-lactide-ε-caprolactone copolymer dissolved therein.

A fluorine-coated stainless steel rod-shaped body having a diameter of 0.6 mm was placed in a glass tube having an inner diameter of 1.1 mm. The uniform solution was poured into the gap between the rod-shaped body and the glass tube. The uniform solution in this state was cooled to −30° C. in a freezer to precipitate a porous body containing the L-lactide-ε-caprolactone copolymer and heparin around the rod-shaped body. The obtained porous body was immersed in an ethanol bath (50 mL) at −30° C. for 12 hours, and then immersed in a water bath (50 mL) at 25° C. for 12 hours for washing.

Thereafter, the porous body was freeze-dried at −40° C. to give a tubular porous body.

Polyglycolide and polylactide were separately dissolved into hexafluoroisopropanol to prepare a hexafluoroisopropanol solution having a polyglycolide concentration of 10% by weight and a hexafluoroisopropanol solution having a polylactide concentration of 10% by weight.

The rod-shaped body with the tubular porous body therearound was used as a collector electrode. The hexafluoroisopropanol solutions were discharged onto the surface of the rod-shaped body using an electrospinning device. At this time, the hexafluoroisopropanol solutions prepared above were charged into two different nozzles, and discharged while rotating the rod-shaped body and reciprocating the nozzles multiple times. Thus, an ultrafine fiber nonwoven fabric layer was formed.

The electrospinning was performed under the conditions of a voltage of −20 kV and a nozzle size of 23 G.

Finally, the rod-shaped body was pulled out to give a tubular artificial blood vessel having an outer diameter of about 1,090 μm and an inner diameter of about 610 μm.

Comparative Example 1

A porous substrate was obtained as in Example 1 except that water without heparin was used as the solvent 1.
(Evaluation)

The porous substrates obtained in the examples and the comparative example were evaluated by the following methods.
(1) Identification of Heparin with Electron Microscope FIG. 1 shows electron micrographs obtained by cutting each of the cylindrical porous substrates obtained in Example 1 and Comparative Example 1 and photographing an area near the center of the cross section at a magnification of 10,000 times.

In the porous substrate obtained in Example 1, as shown in FIG. 1(a), particles that appear to be heparin were adhered to the surface of the porous body containing the L-lactide-ε-caprolactone copolymer. Such particles were not observed in the porous substrate obtained in Comparative Example 1 shown in FIG. 1(b).
(2) Identification of Heparin by Toluidine Blue Staining FIG. 2 shows a photograph of the porous substrates obtained in Example 1 and Comparative Example 1, each stained with toluidine blue.

Figure 2:
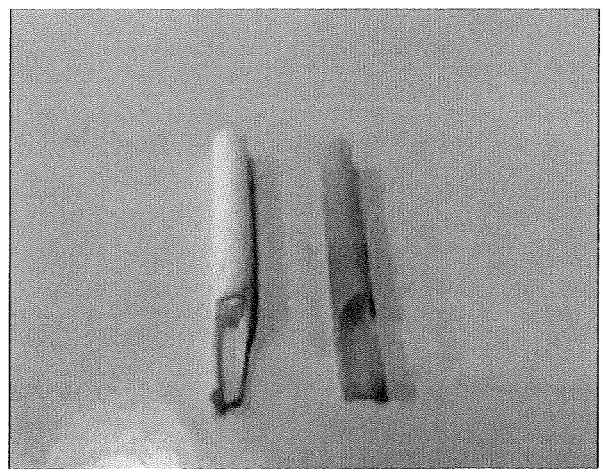
FIG. 2 shows a photograph of the porous substrates obtained in Example 1 and Comparative Example 1 after toluidine blue staining.

As shown in FIG. 2, the porous substrate obtained in Comparative Example 1 was not stained at all (on the left in the photograph), while the porous substrate obtained in Example 1 was stained dark bluish purple as a whole, indicating the presence of heparin (on the right in the photograph).
(3) Identification by Infrared Spectroscopy FIG. 3 shows IR spectra of the porous substrates obtained in Example 1 and Comparative Example 1.

Figure 3:
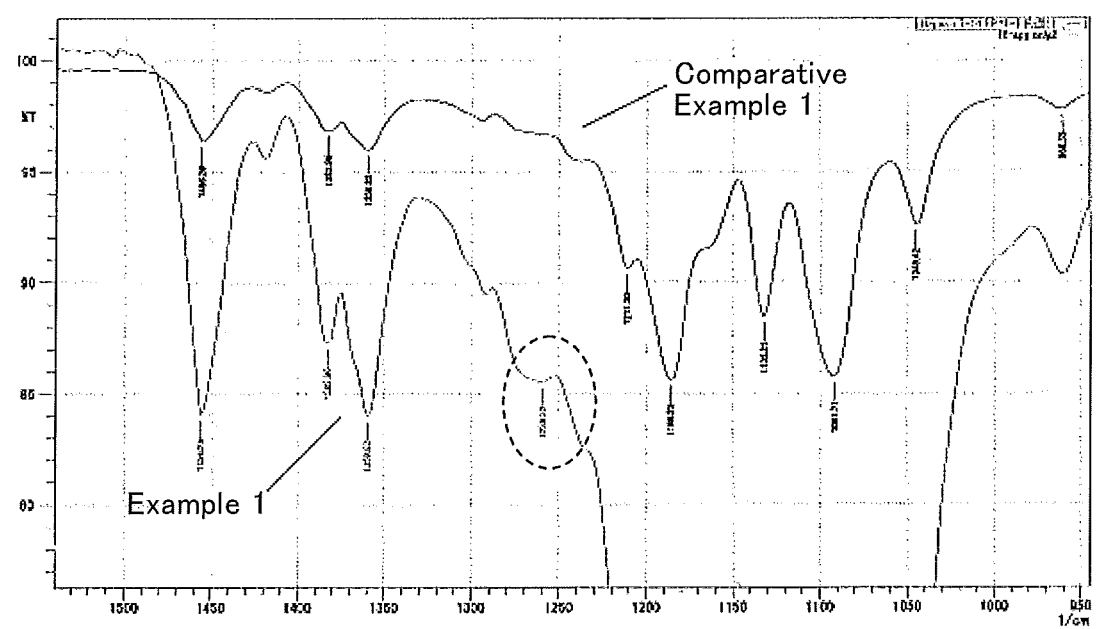
FIG. 3 shows IR spectra of the porous substrates obtained in Example 1 and Comparative Example 1.

As shown in FIG. 3, the IR spectrum of the porous substrate obtained in Example 1 has a peak at 1259 $cm^{-1}$ (peak surrounded by a dotted line) which appears to be derived from heparin. This peak is not found in the IR spectrum of the porous substrate obtained in Comparative Example 1.

INDUSTRIAL APPLICABILITY

The present invention can provide a method for producing a porous substrate containing a bioabsorbable polymer and heparin in a simple manner without use of a surfactant, a porous substrate containing a bioabsorbable polymer and heparin, and an artificial blood vessel.

The invention claimed is:

1. A method for producing a porous substrate containing a bioabsorbable polymer and heparin, comprising:
    a solution preparing step of preparing a heparin-bioabsorbable polymer solution having heparin uniformly dispersed therein and a bioabsorbable polymer dissolved therein, using the bioabsorbable polymer, the heparin, a solvent 1 that is a poor solvent having a lower solvency for the bioabsorbable polymer, a solvent 2 that is a good solvent having a higher solvency for the bioabsorbable polymer and is incompatible with the solvent 1, and a common solvent 3 compatible with the solvent 1 and the solvent 2;
    a precipitating step of cooling the heparin-bioabsorbable polymer solution to precipitate a porous body containing the bioabsorbable polymer and the heparin; and
    a freeze-drying step of freeze-drying the porous body containing the bioabsorbable polymer and the heparin to provide a porous substrate containing the heparin.

2. The method for producing a porous substrate containing heparin according to claim 1, wherein two or more common solvents 3 are used in combination, and a pore size of the resulting porous body is controlled by adjusting a mixing ratio between the two or more common solvents 3.

* * * * *